(12) United States Patent
Cannestra

(10) Patent No.: US 12,213,682 B2
(45) Date of Patent: Feb. 4, 2025

(54) ANTI-SKIVE BONE DRILL

(71) Applicant: INTEGRITY IMPLANTS INC., Palm Beach Gardens, FL (US)

(72) Inventor: Andrew F. Cannestra, Jacksonville, FL (US)

(73) Assignee: INTEGRITY IMPLANTS INC., Jacksonville, FL (US)

( * ) Notice: Subject to any disclaimer, the term of this patent is extended or adjusted under 35 U.S.C. 154(b) by 427 days.

(21) Appl. No.: 17/788,778

(22) PCT Filed: Dec. 23, 2020

(86) PCT No.: PCT/US2020/066871
§ 371 (c)(1),
(2) Date: Jun. 24, 2022

(87) PCT Pub. No.: WO2021/133926
PCT Pub. Date: Jul. 1, 2021

(65) Prior Publication Data
US 2023/0022983 A1      Jan. 26, 2023

Related U.S. Application Data

(60) Provisional application No. 62/954,032, filed on Dec. 27, 2019.

(51) Int. Cl.
*A61B 17/16* (2006.01)
*A61B 17/00* (2006.01)

(52) U.S. Cl.
CPC .... *A61B 17/16* (2013.01); *A61B 2017/00477* (2013.01)

(58) Field of Classification Search
CPC ...................................................... A61B 17/16
See application file for complete search history.

(56) References Cited

U.S. PATENT DOCUMENTS

| | | | |
|---|---|---|---|
| 4,375,341 | A | 3/1983 | Schulze |
| 5,269,785 | A | 12/1993 | Bonutti |
| 5,632,747 | A | 5/1997 | Scarborough et al. |
| 5,851,207 | A | 12/1998 | Cesarone |
| 6,342,057 | B1 | 1/2002 | Brace et al. |

(Continued)

FOREIGN PATENT DOCUMENTS

| | | |
|---|---|---|
| WO | 9325157 | 12/1993 |
| WO | 2021133926 A1 | 7/2021 |

OTHER PUBLICATIONS

Supplementary Search Report issued to European counterpart Application No. 20907951.6 dated May 3, 2024.

(Continued)

*Primary Examiner* — Sameh R Boles
(74) *Attorney, Agent, or Firm* — McNees Wallace & Nurick LLC

(57) ABSTRACT

An anti-skive bone drill assembly is provided, and may be used for spinal surgical procedures. The anti-skive assembly can include a sheath, a drill bit disposed within the sheath, and a mechanism for maneuvering the drill bit within the sheath. The anti-skive assembly, and particularly the sheath, may be mounted in a surgical robot. The anti-skive assembly may be used to side cut a bone to create a flattened surface in an otherwise non-perpendicular bone surface.

11 Claims, 8 Drawing Sheets

(56) References Cited

U.S. PATENT DOCUMENTS

| | | | |
|---|---|---|---|
| 7,985,247 B2 | 7/2011 | Shluzas et al. | |
| RE44,883 E | 5/2014 | Cha | |
| 9,707,016 B2 | 7/2017 | Lee et al. | |
| 9,763,801 B2 | 9/2017 | Lowry et al. | |
| 10,357,257 B2 | 7/2019 | Kostrzewski | |
| 10,357,374 B2 | 7/2019 | Lowry et al. | |
| 10,517,681 B2 | 12/2019 | Roh et al. | |
| 10,765,438 B2 | 9/2020 | Kostrzewski | |
| 10,945,742 B2 | 3/2021 | Kostrzewski | |
| 2003/0055404 A1 | 3/2003 | Moutafis | |
| 2003/0220641 A1 | 11/2003 | Thelen et al. | |
| 2004/0087957 A1* | 5/2004 | Kunzler | A61B 17/17 606/79 |
| 2012/0136358 A1 | 5/2012 | Alleyne | |
| 2016/0151120 A1 | 6/2016 | Kostrzewski et al. | |
| 2019/0350596 A1 | 11/2019 | Kostrzewski | |
| 2021/0022750 A1 | 1/2021 | Kostrzewski | |

OTHER PUBLICATIONS

PCT International Search Report issued to counterpart Application No. PCT/US2020/066871 dated Mar. 8, 2021.

\* cited by examiner

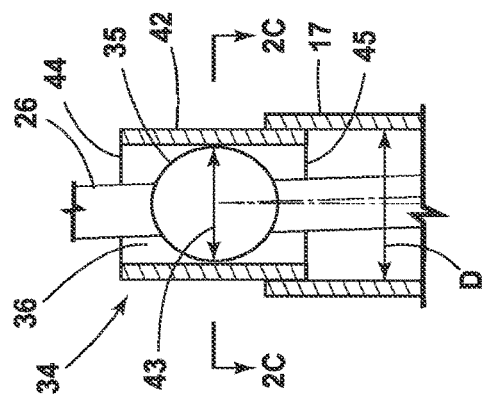
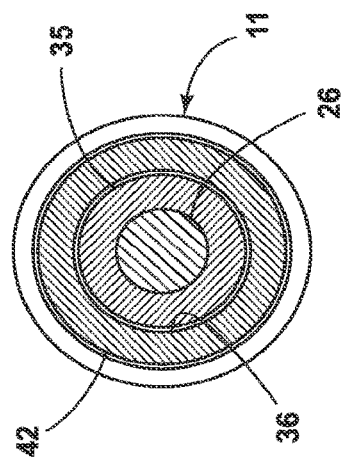
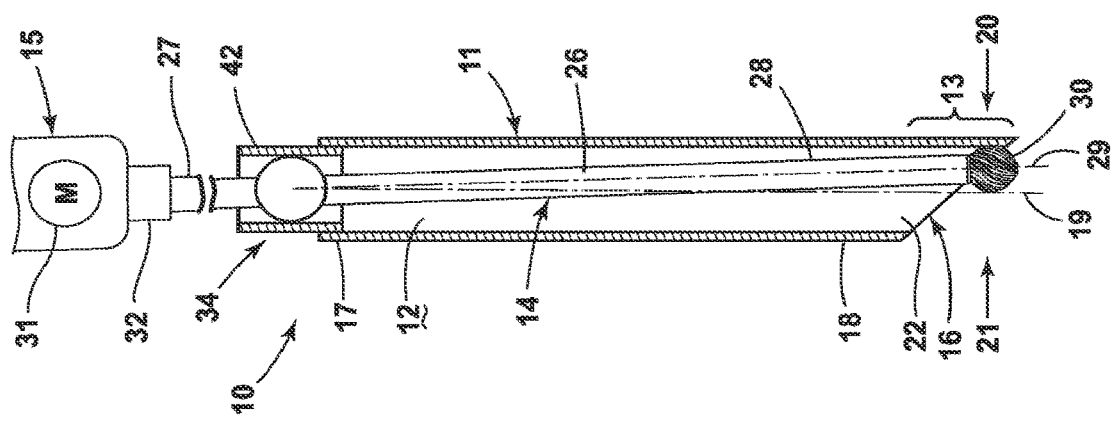
FIG. 2B
FIG. 2C
FIG. 2A

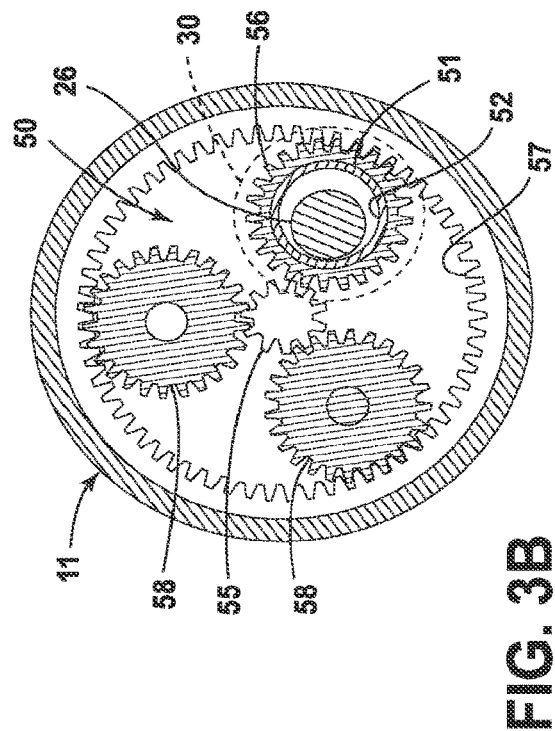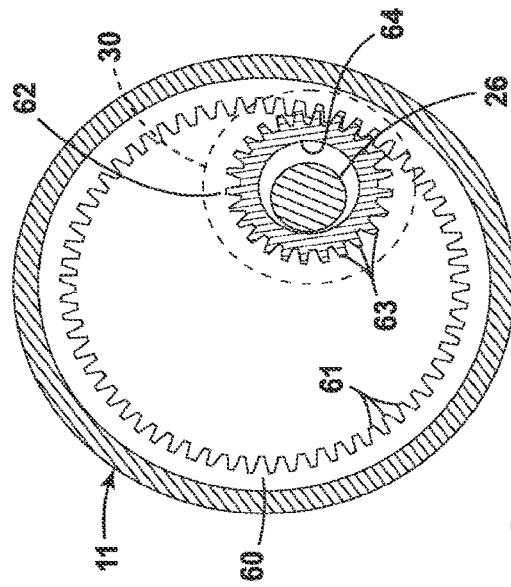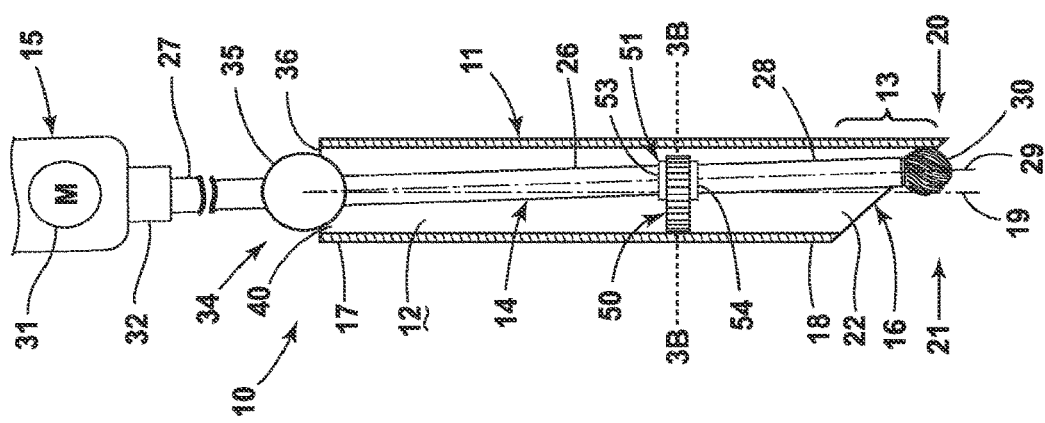

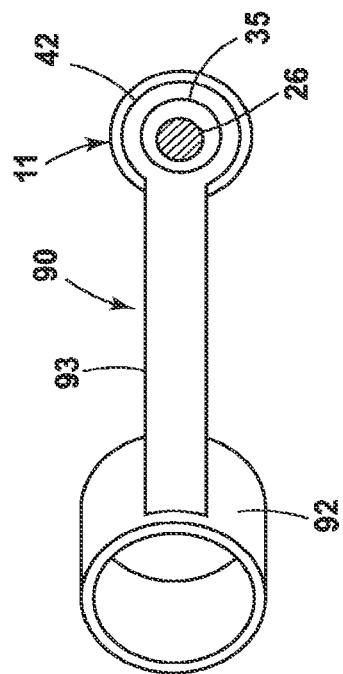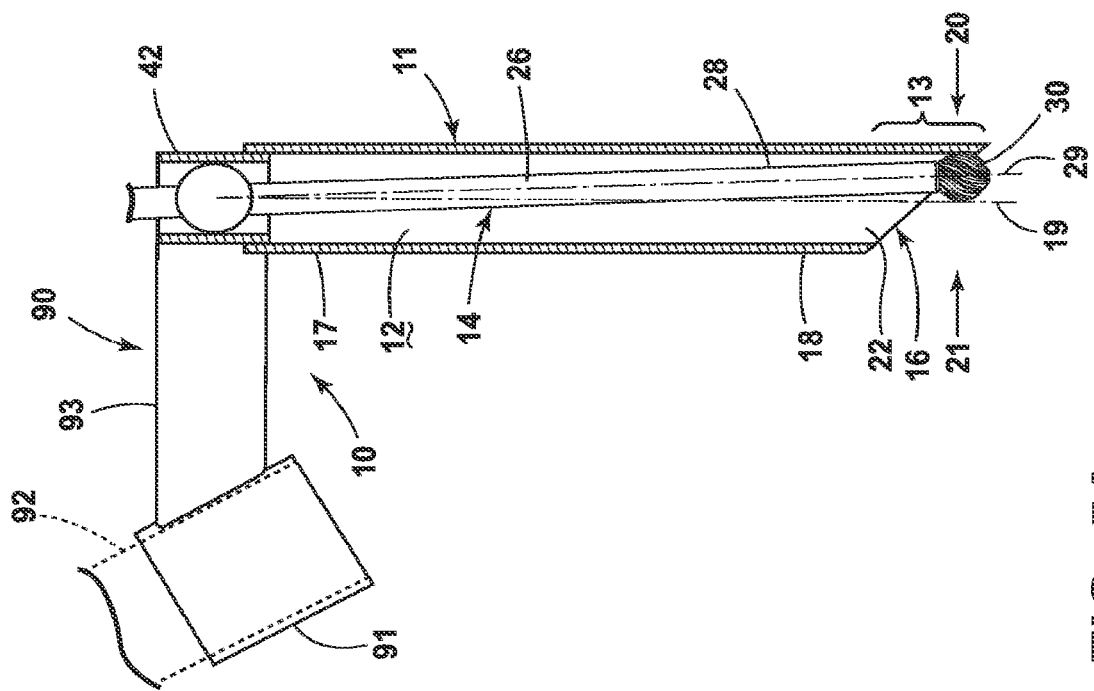
FIG. 5B
FIG. 5A

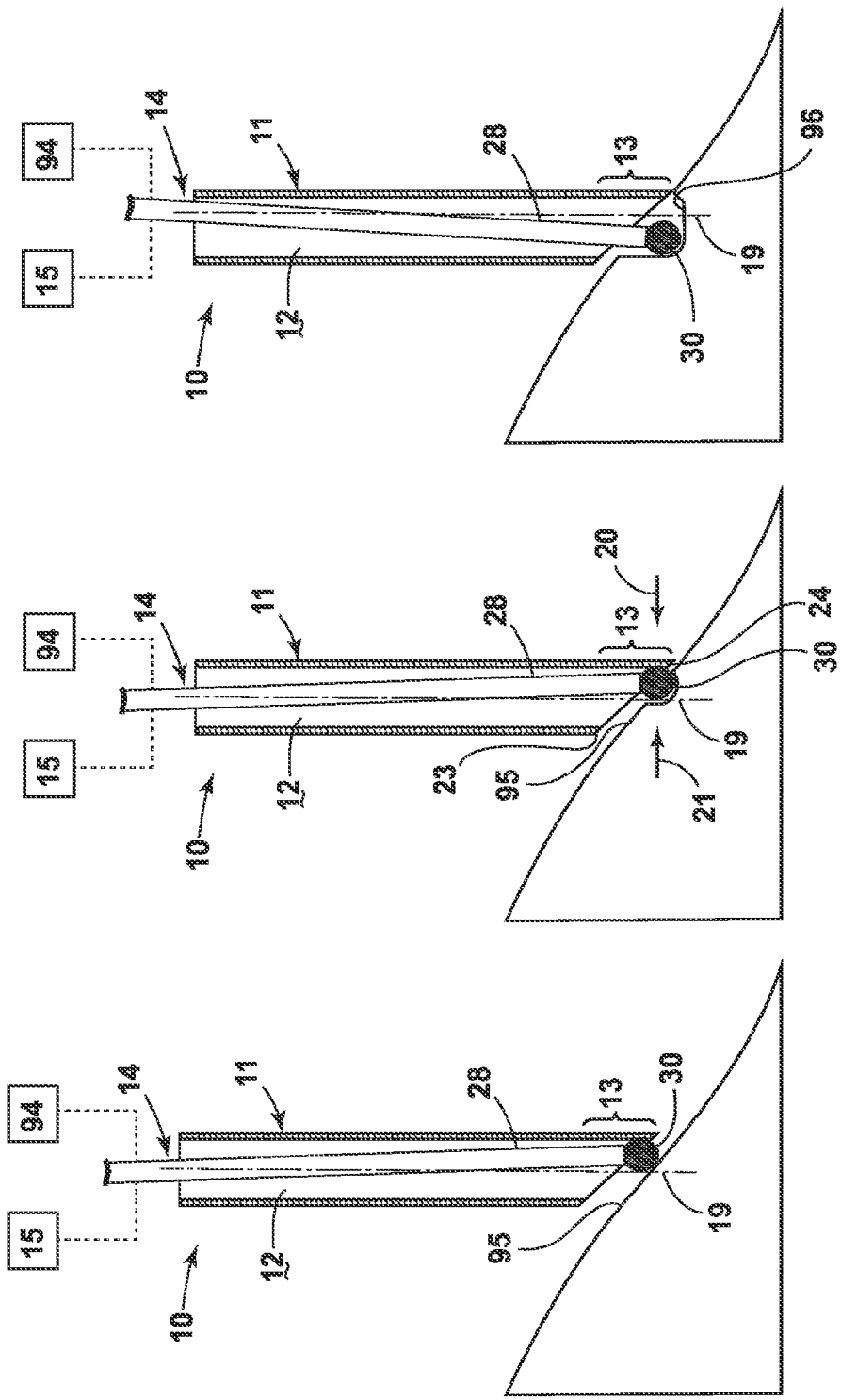

ANTI-SKIVE BONE DRILL

CROSS-REFERENCE TO RELATED APPLICATION(S)

The present application is a 35 U.S.C. 371 National Stage application that claims priority to PCT/US2020/0066871 filed on Dec. 23, 2020, which application claims the benefit under 35 U.S.C. 119(e) to U.S. Provisional Application No. 62/954,032, filed Dec. 27, 2019, each of which is incorporated herein by reference in its entirety.

FIELD OF THE INVENTION

The present invention relates to a bone drill and more particularly an anti-skive bone drill for drilling an angled bone surface flat to prevent walking or "skiving" of a subsequent drill bit.

BACKGROUND OF THE INVENTION

When drilling on an angled bone surface, it is quite common to have skiving of the drill bit prior to the initial bite of the drill into the surface. This skiving can result in a misplaced hole and an inaccurate trajectory. In medicine, and in particular in the field of spinal surgery, the attempt to drill into a non-perpendicular surface can lead to the misplacement of the hole and subsequent harm to the patient. The advent and application of robotics to spinal surgery has magnified the skiving problem. Although a robot provides a trajectory for drilling, if the drill bit is not sufficiently perpendicular to the surface, the subsequent skiving of the drill bit can result in a misplaced hole, despite highly accurate robotic positioning.

The issue is the inconsistency or variability of the surface shape at the docking point of the planned drill site. Because of anatomic variation and pathology, the skiving problem is rather common and is a constant surgical risk in robotic surgery.

SUMMARY

The aforementioned problems are overcome in the present invention in which a side cutting, maneuverable drill bit and sheath assembly is provided that may be used to flatten the docking surface and the planned drill/cannulation site. The assembly may be used to flatten a non-perpendicular surface. After the surface has been flattened, then a subsequent drill bit can initiate the hole without walking or skiving.

In one embodiment, a bone drill assembly comprises a sheath having a distal tip and a longitudinal sheath axis, with a first side of the sheath disposed laterally of the sheath axis in a first direction and a second side of the sheath disposed laterally of the sheath axis in a second direction, the sheath configured to receive a drill bit having a cutting burr, and a manipulation mechanism configured to manipulate the drill bit to move the cutting burr relative to the first and second sides of the sheath, the manipulation mechanism providing lateral displacement of a distal end of the drill bit with respect to the to the sheath axis.

A method of creating a flat surface on a bone is also provided herein. In one embodiment, the method includes positioning a bone drill assembly adjacent a bone surface, the assembly including a sheath having a sheath axis, a drill bit within the sheath, and a manipulation mechanism supporting the drill bit within the sheath, the sheath axis being non-perpendicular to the bone surface, and maneuvering the drill bit within the sheath such that the drill bit moves laterally with respect to the sheath axis, whereby the drill bit removes bone laterally with respect to the sheath axis thereby creating the flat surface.

These and other advantages and features of the invention will be more fully understood and appreciated by reference to the description of the current embodiment and the drawings.

BRIEF DESCRIPTION OF THE DRAWINGS

FIG. 2A is a schematic side view of an assembly according to a second embodiment of disclosure, the assembly including a ball and socket joint.

FIG. 2B is a close-up view of the ball and socket joint of the assembly of FIG. 2A.

FIG. 2C is a cross-sectional view of the assembly taken through line 2C-2C of FIG. 2B.

FIG. 3A is a schematic side view of the assembly according to a third embodiment of disclosure, the assembly including a gear drive mechanism.

FIG. 3B is a cross-sectional view of the assembly taken through line 3B-3B of FIG. 3A.

FIG. 3C is a cross-sectional view of another embodiment of a gear drive mechanism for the assembly of FIG. 3A.

FIG. 5A is a schematic side view of the assembly according to a fifth embodiment of disclosure, the assembly comprising an adaptor coupling a sheath to a robotic arm.

FIG. 5B is a schematic top view of the assembly of FIG. 5A.

FIGS. 6A, 6B, and 6C show a method of using an assembly to flatten an angled or non-perpendicular bone surface The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

DETAILED DESCRIPTION

Figure 1A:
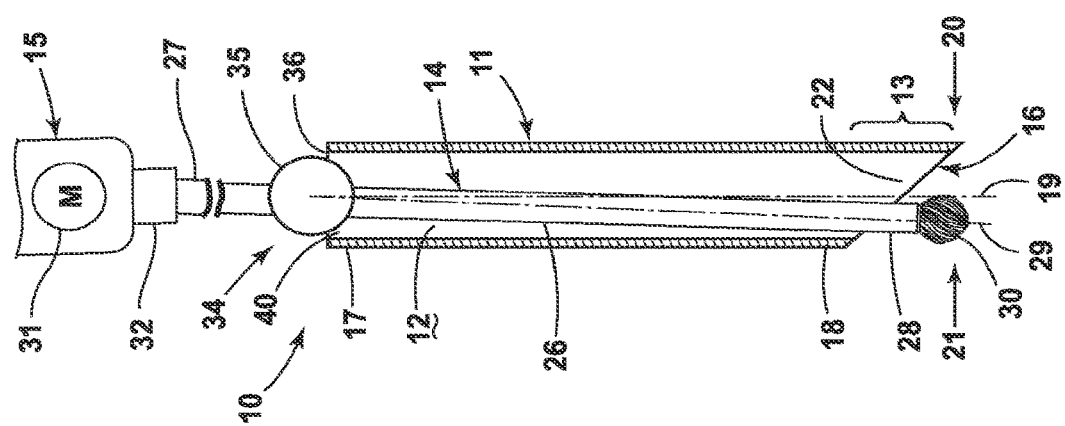
FIG. 1A is a schematic side view of an assembly for flattening an angled or non-perpendicular bone surface according to a first embodiment of disclosure, the assembly including a drill bit and a sheath, and showing the drill bit in a first position within the sheath.

Before the embodiments of the invention are described, it is to be understood that the invention is not limited to the details of operation or to the details of construction; and the arrangement of the components set forth in the following description or illustrated in the drawings. The invention may be implemented in various other embodiments and may be practiced or carried out in alternative ways not expressly disclosed herein.

In addition, it is to be understood that the phraseology and terminology used herein are for the purpose of description and should not be regarded as limiting. The use of "including" and "comprising" and variations thereof encompasses the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one or more of X, Y or Z individually, and any combination of any one or more of X, Y and Z, for example, X, Y, Z; X, Y; X, Z; and Y, Z.

It is noted that embodiments of the assembly are schematically represented throughout the figures, and components thereof are not necessarily drawn to scale relative to each other, unless otherwise noted. Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

An assembly including a sheath 11 and an internal drill bit 14 for flattening an angled (non-perpendicular) bone surface is illustrated in the drawings and generally designated 10. Referring to FIG. 1, in a first embodiment, the sheath 11 is tubular and includes an interior channel 12, with a distal tip 13 of the tubular sheath 11. The distal tip 13 has an end shape 16 configured to expose the drill bit 14 on only a portion of the diameter of the sheath 11, thereby protecting tissue on the opposite portion of the diameter from exposure to the drill bit 14. For example, the distal tip 13 may expose the drill bit 14 on approximately half of the diameter of the sheath 11, thereby protecting tissue on the opposite half of the diameter from exposure to the drill bit 14.

The sheath 11 has a proximal end 17 and a distal end 18, and defines a longitudinal axis 19. A first side 20 of the sheath 11 is disposed laterally of the sheath axis 19 in a first direction and a second side 21 of the sheath 11 is disposed laterally of the sheath axis 19 in a second direction.

The tubular channel 12 of the sheath 11 is sized for insertion of the drill bit 14. The sheath 11 is preferably fabricated of a single piece, may be fabricated of multiple pieces. The tubular channel 12 preferably defines a single continuous tubular structure. In some embodiments, the sheath 11 can be sized for insertion through a cannulated guide, and the like. For clarity, the sheath 11 is shown cut-away in FIGS. 1A-1B.

Figure 1B:
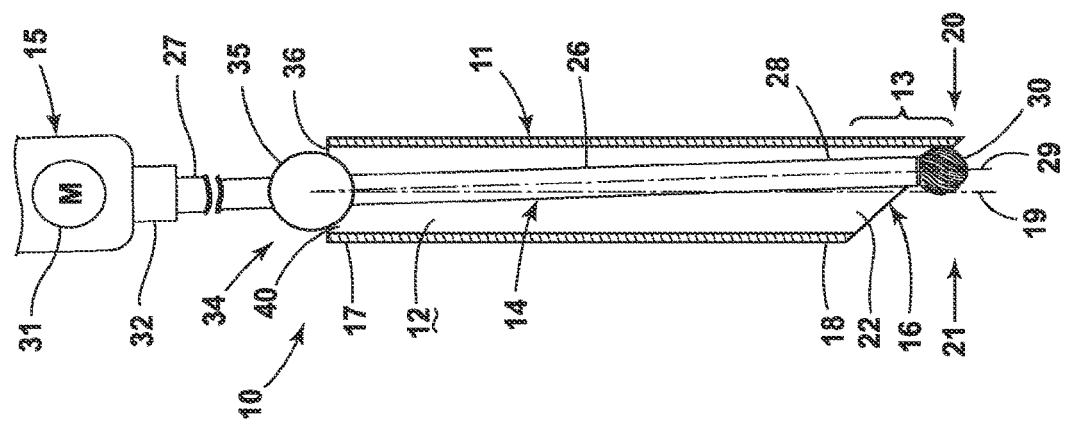
FIG. 1B is a schematic side view of the assembly of FIG. 1A, showing the drill bit in a second position within the sheath.

The distal tip 13 of the sheath 11 is disposed at the distal end 18 thereof and defines a sheath opening 22. The distal tip 13 can have an end shape 16 that is non-perpendicular to the axis 19 of the shaft, e.g. is not flat. The distal tip 13 of the sheath 11 can be angled, tapered, curved or otherwise shaped to provide a non-perpendicular or non-flat tubular end shape 16 on the distal end 18 of the sheath 11, for example as shown in the embodiment of FIG. 1A-1G. It is noted that sections of the end shape 16 may be flat or perpendicular to the axis 19 of the sheath 11, for example as shown in the embodiment of FIG. 1H. However, the overall end shape 16 around the circumference of the sheath is not flat or perpendicular. Particularly, a portion of the end shape 16 on the first side 20 of the sheath 11 is preferably distal of a portion of the end shape 16 on the second side 21 of the sheath 11, along the axis 19 of the sheath 11. An end shape 16 with distal and proximal portions can also allow for seating the distal tip 13 of the sheath 11 in close proximity to an angled bone surface.

Figure 1C:
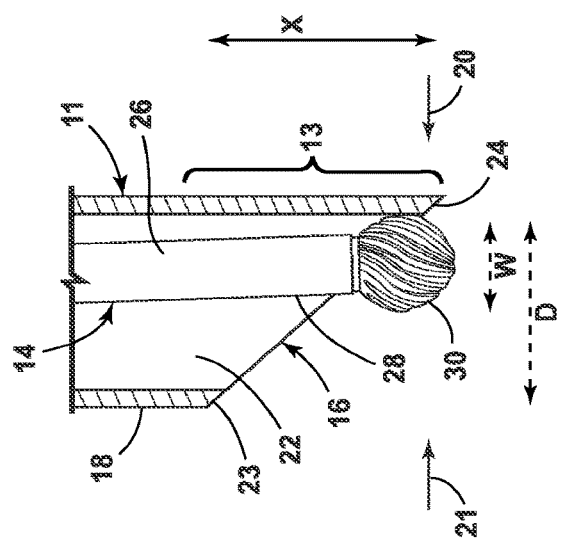
FIG. 1C is a close-up view of the distal tip the assembly in the position shown in FIG. 1A.
Figure 1D:
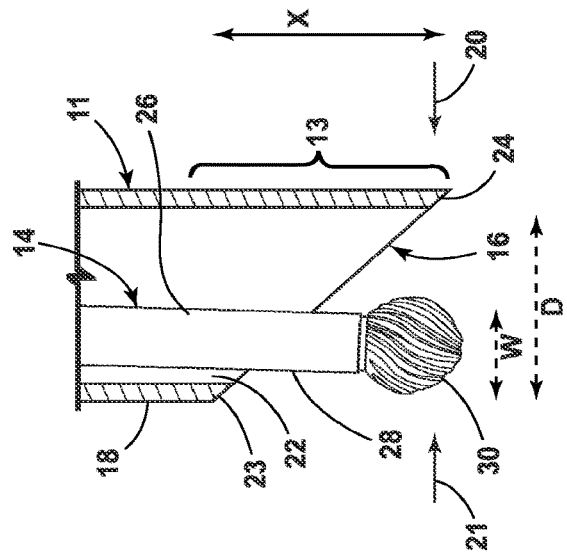
FIG. 1D is a close-up view of the distal tip the assembly in the position shown in FIG. 1B.
Figure 1E:
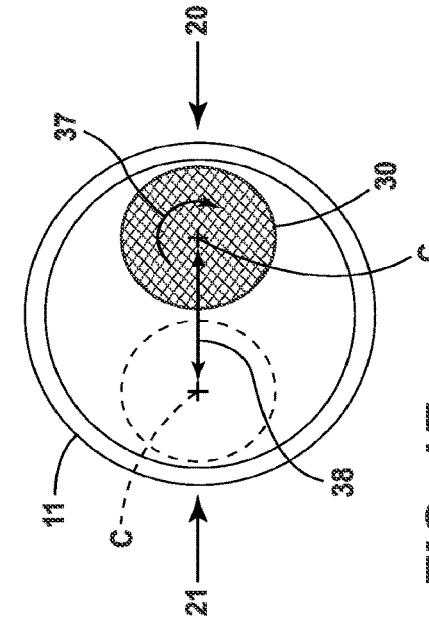
FIG. 1E is a bottom view of the assembly of FIG. 1A showing translational movement of the drill bit.
Figure 1F:
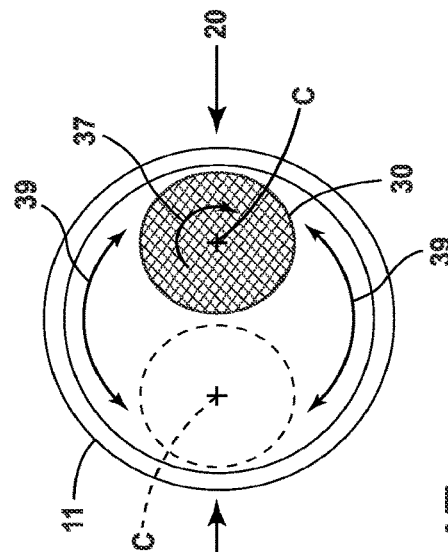
FIG. 1F is a bottom view of the assembly of FIG. 1A showing orbital movement of the drill bit.
Figure 1G:
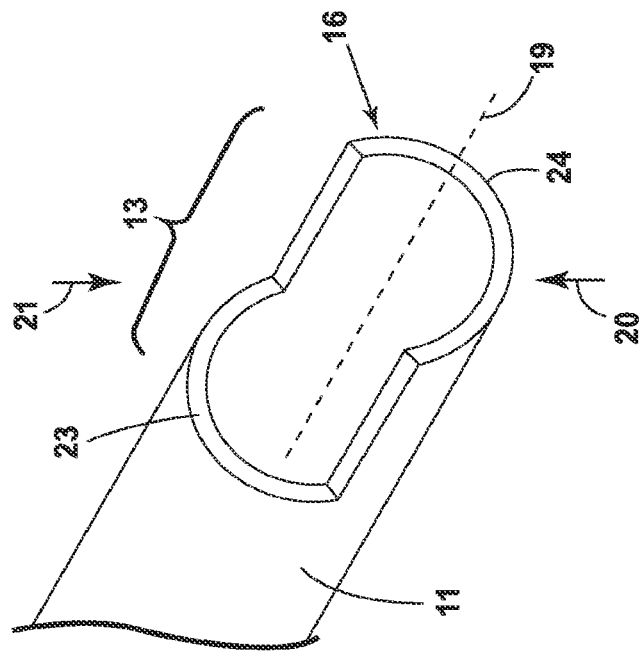
FIG. 1G is a perspective view of a distal tip of the sheath for the assembly of FIG. 1A.
Figure 1H:
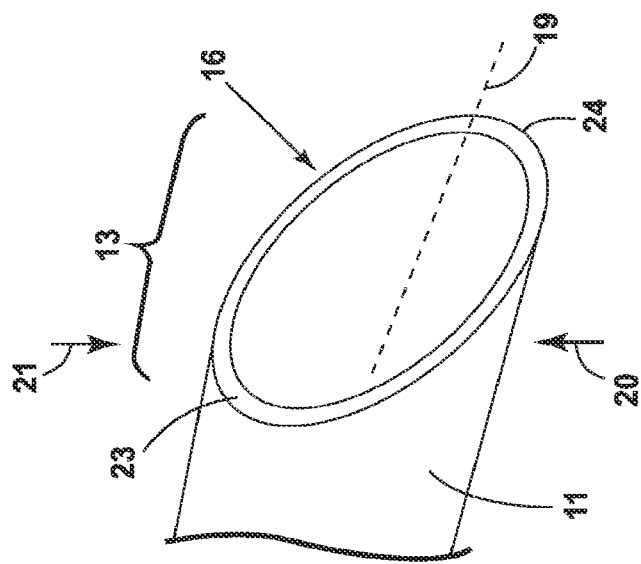
FIG. 1H is a perspective view of another embodiment of a distal tip of the sheath for the assembly of FIG. 1A.

Referring to FIGS. 1C, 1D, and 1G in some embodiments, the distal tip 13 of the sheath 11 can have an end shape 16 with a tip distal edge 24 on the first side 20 of the sheath 11 and a tip proximal edge 23 on the second side 21 of the sheath. The tip distal edge 24 is disposed distally of the tip proximal edge 23 along the axis 19, and in some embodiments, the tip distal edge 24 can define a distal-most point of the sheath 11. The first side 20 of the sheath 11 includes the tip distal edge 24 can defines the first side 20 of the sheath 11, along which the cutting burr 30 of the drill bit 14 is disposed in the drill position shown in FIG. 1C. This position exposes bone and tissue on the first side 20 of the sheath 11 to the burr 30, thereby protecting tissue on the second side 21 from exposure to the burr 30. The tip proximal edge 23 can define the second side 21 of the sheath 11, along which the burr 30 is disposed in the drill position shown in FIG. 1D. This position exposes bone and tissue on the second side 21 of the sheath 11 to the burr 30, thereby protecting tissue on the first side 20 from exposure to the burr 30.

In the embodiment of FIG. 1G, the distal tip 13 of the sheath 11 has an angled end shape 16 defining the tip proximal edge 23 and tip distal edge 24 along sections of the end shape 16 that are not flat or non-perpendicular to the axis 19 of the sheath 11. In the embodiment FIG. 1H, the distal tip 13 of the sheath 11 has a notched end shape 16 defining the tip proximal edge 23 and tip distal edge 24 along sections of the end shape 16 that are flat or perpendicular to the axis 19 of the sheath 11.

At least a portion of the burr 30 is disposed on a first side of the axis 19 in FIG. 1A disposed toward the first side 20 of the sheath 11. In this position, the burr 30 can be disposed toward the tip distal edge 24 as shown in FIG. 1C. In some embodiments, a geometric center C of the burr 30 can lie between the axis 19 and the first side 20 in this position. In the embodiment illustrated, substantially the entire burr 30 is disposed on the first side of the axis 19 in the drill position of FIGS. 1A and 1C. By "substantially the entire burr 30", at least 70% of the burr 30, alternatively at least 80% of the burr 30, alternatively at least 95% of the burr 30, alternatively the entire burr 30 may be disposed on the first side of the axis 19 in the drill position of FIGS. 1A and 1C.

At least a portion of the burr 30 is disposed on a second side of the axis 19 in FIG. 1B disposed toward the second side 21 of the sheath 11. In this position, the burr 30 can be disposed toward the tip proximal edge 23 as shown in FIG. 1D. In some embodiments, the geometric center C of the burr 30 can lie between the axis 19 and the second side 21 in this position. In the embodiment illustrated, substantially the entire burr 30 is disposed on the second side of the axis 19 in the drill position of FIGS. 1B and 1D. By "substantially the entire burr 30", at least 70% of the burr 30, alternatively at least 80% of the burr 30, alternatively at least 95% of the burr 30, alternatively the entire burr 30 may be disposed on the second side of the axis 19 in the drill position of FIGS. 1B and 1D.

In some embodiments, the distal tip 13 of the sheath 11 can be angled, as best seen in FIGS. 1C and 1D, from the tip proximal edge 23 to the tip distal edge 24. Other end shapes 16 defining at least one tip proximal edge 23 and at least one tip distal edge 24 are possible.

In some embodiments, a distance X between the tip proximal edge 23 and the tip distal edge 24, measured along the longitudinal axis 19 of the sheath 11, can be at least 50% of a width W of the burr 30. Alternatively, the distance X can be at least 75% of the width W of the burr 30. Alternatively, the distance X at least 100% of the width W of the burr 30 (e.g., distance X is equal to or greater than width W). For a ball-shaped burr 30 as shown in the drawings, the width W of the burr 30 can be the diameter of the burr 30. The width W of the burr 30 can be measured as the maximum dimension of the burr 30 perpendicular to the drill axis 29.

The inner diameter D of the sheath 11 is preferably greater than the width W (or diameter) of the burr 30 in order to allow for a range of movement of the burr 30 within the distal tip 13. The inner diameter D may be, for example, at least twice the width W of the burr 30.

Returning to FIGS. 1A and 1B, the drill bit 14 has a proximal end 27 and a distal end 28, with a drill shaft 26 extending along and defining a longitudinal axis 29 of the drill bit 14. The drill bit 14 can include a cutting burr 30 at the distal end 28 thereof. The cutting burr 30 can be fluted or otherwise shaped with sharp edges for cutting into a bone surface at the drill bit 14 rotates about the longitudinal axis 29. The cutting burr 30 can be a side-cutting having a ball shape with a rounded end, a flat end, or other suitable configuration for flattening an angled bone surface. The burr 30 can be made out of medical grade carbide or other suitable medical grade material.

The drill bit 14 may attach to a standard power drill 15 or other motorized drive unit having a motor 31. The power drill 15 is depicted schematically in FIGS. 1A-1B. The drill shaft 26 is coupled to the power drill 15 at the proximal end 27, such as by being clamped by or otherwise engaged by a chuck 32 of the power drill 15 that is driven by the motor 3 and rotates the drill bit 14 about the longitudinal axis 29. To couple the drill bit 14 to the power drill 15, the drill bit 14 is loaded into the sheath 11. The drill bit 14 may be bottom-loaded by first inserting the drill bit 14 through the sheath opening 22, or top-loaded. In either case, the drill bit 14 is inserted until the proximal end 27 of the drill bit 14 extends from the proximal end 17 of the sheath 1. The proximal end 27 is then engaged by the chuck 32.

In operation, the distal end 28 of the drill bit 14 may move within the sheath 11 in order to move the burr 30 relative to the first and second sides 20, 21 of the sheath 11. Such movement may include moving the burr 30 away from the first side 20 of the sheath 11, i.e. toward the second side 21. FIGS. 1B and 1D depict one position of the drill bit 14 in which the burr 30 is disposed at the second side 21. Such movement may include moving the burr 30 away from the second side 21 of the sheath 11, i.e. toward the first side 20.

FIGS. 1A and 1C depict one position of the drill bit 14 in which the burr 30 is disposed at the first side 20. During movement of the burr 30, the power drill 15 also rotates the drill bit 14 about its longitudinal axis 29. As the drill bit 14 moves, the rotating burr 30 can shave down an angled bone surface to form a flat bone surface.

The sheath 11 has an inner diameter D perpendicular to the longitudinal axis 19. The inner diameter D of the sheath 11 can limit the movement of the drill bit 14, thereby providing controlled exposure of the burr 30 to the bone surface and protecting bystander tissue (lateral and superficial) from the burr 30. The maximum distance the drill bit 14 may move in any direction can accordingly be approximately the equal to the inner diameter D of the sheath 11. Thus, the drill bit 14 may flatten an underlying bone surface by traversing the bone surface area under the constraint of the sheath 11.

The assembly 10 has a mechanism configured to manipulate the drill bit 14 within the sheath 11 to move the burr 30 relative to the first and second sides 20, 21 of the sheath 11. Details of some embodiments of the manipulation mechanism are discussed below. Various types of manipulation of the drill bit 14 are possible, including translational, orbital, or a combination of translation and orbital manipulation. Translational manipulation comprises moving the distal end 28 of the drill bit 14 in a straight-line path within the sheath 11 to translate the burr 30 within the distal tip 13. Orbital translation comprises moving the distal end 28 of the drill bit 14 in a conical path within the sheath 11 to circulate or orbit the burr 30 within the distal tip 13. During the manipulation, the power drill 15 can rotate the drill bit 14 about its longitudinal axis 29. Thus, depending on the configuration, the burr 30 may travel in a straight-line path, a circular path, an orbital path, or a combination thereof, while simultaneously rotating about the drill axis 29.

FIGS. 1E and 1F depict examples of the spatial manipulation of the drill bit 14 within the sheath 11. In both examples, the drill bit 14 can be rotating about its longitudinal axis 29 as indicated by arrow 37. FIG. 1E shows one example of translation of the burr 30 within the distal tip 13, as indicated by arrow 38. While only one translation direction is shown, it is understood that, depending on the manipulation mechanism, multiple translation directions may be possible, including up to any direction within a plane perpendicular to the sheath axis 19. FIG. 1F shows one example of circulating or orbiting of the burr 30 within the distal tip 13, as indicated by arrows 39. Depending on the manipulation mechanism, the burr 30 may move in a clockwise direction around the sheath 11, a counterclockwise direction around the sheath 11, or in either direction. It is also understood that, while a circular orbit is shown, the burr 30 may move in a non-circular orbit as well. Furthermore, some embodiments of the manipulation mechanism may permit the burr 30 to be moved in a combination of translational and orbital movements.

The mechanism for manipulating the drill bit 14 can be operated under automated control (e.g. via automatic input in a controlled mechanical fashion), under manual control (e.g. via manual input or under direct operator control), or under a combination automated and manual control (e.g. via robotics-assisted instrumentation or handled smart instrumentation, for example). Automatic input control can provide highly consistent and accurate results. Manual input control gives the operator control over the motion input, and thus, the motion output at the burr 30. The operator can start and stop the motion, can reverse motion direction, and can change the speed of the motion. Using a combination of operator and robotic control combines the skill of the operator with the accuracy associated with robotics.

In the embodiment of FIG. 1, the mechanism includes a ball and socket joint 34 including a ball 35 connected with the drill bit 14 and a socket 36 connected with the sheath 11, preferably concentric with the axis 19 of the sheath 11, and which partially surrounds and receives the ball 35. As used herein, "connected with" and variations thereof is used herein in the broadest sense to mean and encompass the notions of being formed or integrated with, mounted or attached to, or otherwise joined. The position of the ball 35 relative to the burr 30 can be calibrated with the distance between the socket 36 and the distal tip 13 of the sheath 11, such that when the ball 35 is in register with the socket 36, the burr 30 is located at the distal tip 13 of the sheath 11.

The ball 35 has several degrees of motion within the socket 36, while at the same time the socket 36 can restrict or prevent translation of the ball 35 in any direction. The degrees of motion allow the drill bit 14 to rotate about the drill axis 29 (as indicated by arrow 37) for rotation of the cutting burr 30 as powered by the motor 31, while an operator provides manual input to manipulate the ball 35 within the socket 36 in order to move the burr 30 relative to the sides 20, 21 of the sheath 11. During some procedures, the operator can provide manual input to rotate the ball 35 side-to-side in order to translate the burr 30 from the first side 20 to the second side 21 (and vice versa) as indicated by arrow 38. During some procedures, the operator can provide manual input to swivel the ball 35 in order to orbit the burr 30 from the first side 20 to the second side 21 (and vice versa) as indicated by arrow 39. During some procedures, the operator can provide a combination of such manual input to manipulate the burr 30 within the inner circumference of the distal tip 13 of the sheath 11.

In the embodiment shown, where the mechanism is controlled manually, the socket 36 can be formed by an open proximal end 40 of the sheath 11, with the ball 35 having a diameter larger than the inner diameter D of the sheath 11 and the ball 35 simply resting on the open proximal end 40 of the sheath 11. The ball 35 can have low friction with the sheath 11 in order to reduce resistance therebetween, such as by being manufactured from materials having low coefficient of friction or using lubricants. In other embodiments, movement of the ball 35 within the socket 36 can be operated under automated control (e.g. via automatic input in a controlled mechanical fashion).

The ball 35 can be integrated with the drill shaft 26. The drill bit 14 can be loaded through the open proximal end 40 of the sheath 11 until the ball 35 reaches the open proximal end 40, i.e. is received by the socket 36. Alternatively, the ball 35 can be provided separately from the drill bit 14, and provided with means for connecting the ball 35 to the drill bit 14. For example, the ball 35 can comprise an opening extending through the diameter of the ball 35. The drill shaft 26 can be slid through the opening and the ball 35 secured at a fixed axial position on the drill shaft 26. The latter configuration is useful in embodiments where the drill bit 14 is bottom-loaded into the sheath 11 and/or in embodiments where an existing drill bit 14 is adapted or modified for use with the assembly 10. In such a case, the ball 35 can allow a standard drill bit to be loaded into the assembly 10, such that the assembly 10 comprises the sheath 11 and ball 35. In this case, the assembly can adapt or retrofit an existing drill to operate as described herein.

In some embodiments, the mechanism for manipulating the drill bit 14 can support or suspend the drill bit 14 within the sheath 11, as well as providing lateral displacement of the burr 30. For example, the ball 35 of FIGS. 1A-1B can effectively suspend the drill bit 14 within the sheath 11. In other embodiments, the drill bit 14 can be supported or suspended within the sheath 11 by another structure.

While not shown herein, the sheath 11 can pass through a robotic arm of a robotics-assisted surgical system. Such systems provide a robotic arm that have attachment points for guides and sheaths. The robot provides a stable calibrated trajectory, and the attached robotic arm provides a cannula through which drills, sheaths, wires, cannula and screws can be passed. With these systems, the power drill 15 is typically a handheld, battery-powered or electric drill.

FIGS. 2A-2C show a second embodiment of the assembly 10, where like elements are referred to with the same reference numerals. The assembly 10 comprises a similar ball and socket joint 34, having a different configuration for the socket 36. In the second embodiment, the socket 36 can be included on a separate member 42 attachable at the proximal end 17 of the sheath 11. As such, the socket member 42 can adapt or retrofit a standard tubular sheath for use with the assembly 10, rather than requiring a sheath that is sized in relation to the ball 35. This also provides the freedom for the sheath diameter D to be larger than an inner diameter 43 of the socket 36, providing a greater range of movement for the burr 30 at the distal tip 13. This can also permit the ball 35 to have a smaller diameter than the inner diameter D of the sheath 11. The surface of the ball 35 can have low friction with the socket member 42 in order to reduce resistance therebetween, such as by being manufactured from materials having low coefficient of friction or using lubricants.

The socket member 42 can have an open proximal end 44 and an open distal end 45, with the socket 36 disposed between the ends 44, 45. The socket member 42 can be attached to the sheath 11 using any suitable means, such as, for example via an interference fit with the open proximal end 40 of the sheath 11. While a socket member 42 having a cylindrical shape is shown, other configurations are possible, including a spherical or tapered shape.

FIGS. 3A and 3B show a third embodiment of the assembly 10, where like elements are referred to with the same reference numerals. In the third embodiment, the assembly 10 includes a gear drive 50 inside the sheath 11 that produces a controlled orbital motion of the drill bit 14 to move the burr 30 within the distal tip 13. The gear drive 50 may orbit the drill shaft 26 to produce conical movement of the distal end 28, thereby moving the burr 30 relative to the sides 20, 21 of the sheath 11

In certain embodiments, the assembly 10 can include a drill sheath 51 defining a tubular channel 52 sized for insertion of the drill bit 14. The drill sheath 51 in turn is received within the tubular channel 12 of the outer sheath 11. The sheath 51 has a proximal end 53 and a distal end 54, and defines a longitudinal axis that can be generally coaxial with the longitudinal axis 29 of the drill bit 14.

The gear drive 50 can engage the drill sheath 51 in order to move the drill sheath 51 internally in the outer sheath 11, and thereby moving the drill bit 14. The gear drive 50 may move the distal end 54 of the drill sheath 51 in a conical path, in turn producing deflection of the distal end 28 of the drill bit 14, thereby circulating or orbiting the burr 30 within the distal tip 13 relative to the sides 20, 21 of the outer sheath 11. In other embodiments, the gear drive 50 can include directly engage the drill bit 14, or otherwise be configured to move the drill bit 14 without the use of drill sheath 51.

The gear drive 50 can include a planetary gear system that provides an orbital motion to the distal end 28 of the drill bit 14. In such gear system, a sun gear 55 can be mounted within the sheath 11 along the longitudinal axis 19 for rotation about the axis 19. A planet gear 56 is fixed on the drill sheath 51 and meshed with the sun gear 55. The planet gear 56 rolls around the sun gear 55 on the inside of a ring gear 57, which is fixed and non-rotatable on the interior of the sheath 11, producing orbital motion of the burr 30. The gear drive 50 may include additional gears, such as, but not limited to, additional planet gears 58.

The sun gear 55 can be rotated via manual input (e.g. under dirt operator control) or automatic input (e.g., under automated control). Depending on the type of input, the sun gear 55 or one of the planet gears 56, 58 coupled with a suitable drive input to provide driving force the other gears of the gear drive 50. For a manual input mechanism, an operator provides manual input to move the planet gear 56 around the sun gear 55, thereby producing orbital motion of the burr 30. For an automatic input mechanism, a motorized drive unit (not shown) having a motor can be coupled with the sun gear 55 to provide drive input to rotate the sun gear 55, which in turn rolls the planet gear 56 around the inside of the ring gear 57.

The drill bit 14 and sheath 11 can include a ball and socket joint 34 as previously described, with the ball 35 supporting the drill bit 14 at the proximal end 17 of the sheath 11. Optionally, the drill bit 14 and sheath 11 can be calibrated using ball 35 as previously described.

The sheath 11 comprises the gear drive 50, which may be disposed within a gear casing (not shown) within the sheath 11. The drill bit 14 can be loaded from the bottom or distal end of the sheath 11, through the drill sheath 51, until the proximal end 27 of the drill bit 14 extends out the proximal end 17 of the sheath 11 to mate to the drill chuck 32.

In some embodiments, in order to load the sheath 11, the drill bit 14 can be provided in two or more sections, with one section being top-loaded for connection with the gear drive 50 and another section being bottom-loaded for connection with the gear drive. There may be a standard loading mechanism to load a drill bit 14 and a standard loading mechanism to load the gear drive 50.

In another embodiment shown in FIG. 3C, the gear drive 50 includes an annular gear 60 mounted within the sheath 11 and having teeth 61 arranged in a circular ring, and a pinion 62 having teeth 63 meshed with the teeth 61 of the annular gear 60. The pinion 62 has an opening 64 through which the drill shaft 26 (or drill sheath 51 surround the drill shaft 26) passes. The pinion 62 rolls around the inside of the annular gear 60, which is fixed and non-rotatable on the interior of the sheath 11, producing orbital motion of the burr 30. The gear drive 50 may include additional gears, such as, but not limited to, additional planet gears 58.

The pinion 62 can be coupled with a suitable drive input for rotation about the inside of the annular gear 60. For example, the pinion 62 can be rotated via manual input (e.g. under dirt operator control) or automatic input (e.g., under automated control). For an automatic input mechanism, a motorized drive unit (not shown) having a motor can provide drive input to rotate the pinion 62.

Figure 4C:
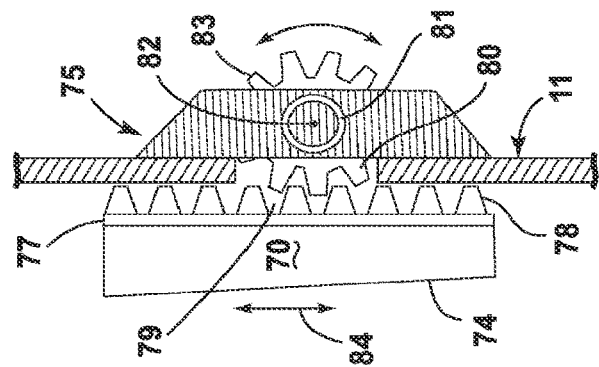
FIG. 4C is a close-up view of a rack and pinion actuator of the assembly of FIG. 4A-4B.
Figure 4B:
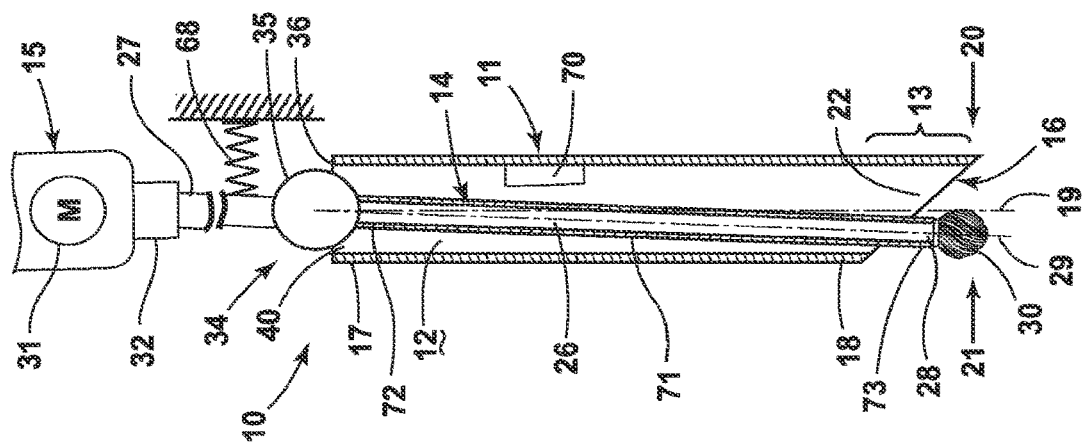
FIG. 4B is a schematic side view of the assembly of FIG. 4A, showing the drill bit in a second position within the sheath.
Figure 4A:
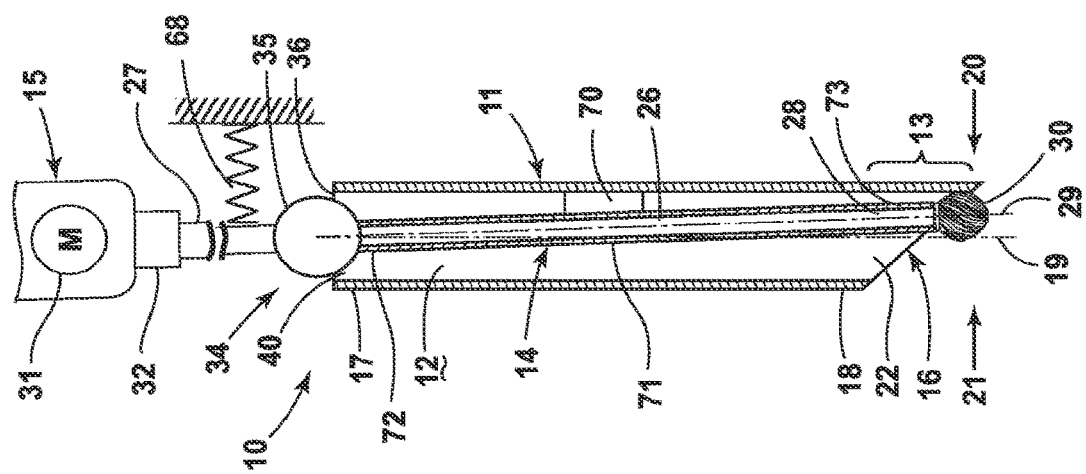
FIG. 4A is a schematic side view of the assembly according to a fourth embodiment of disclosure, the assembly including a mechanically driven block, and showing the drill bit in a first position within the sheath.

FIGS. 4A-4C show a fourth embodiment of the assembly 10, where like elements are referred to with the same reference numerals. In the fourth embodiment, the assembly 10 has a mechanism that deflects the drill bit 14 in a controlled fashion in a straight-line path within the sheath 11 to translate the burr 30 within the distal tip 13. The manipulation mechanism includes a block 70 inside the sheath 11 configured to move axially along the sheath axis 19 to produce deflection of the distal end 28 of the drill bit 14 within the sheath 11, thereby translating the cutting burr 30 in a straight-line path. The block 70 can move axially within the channel 12 to deflect the drill bit 14 internally in the sheath 11. The block 70 may travel along the drill shaft 26 in either axial direction to produce deflection of the distal end 28, thereby moving the burr 30 toward the second side 21 of the sheath 11.

One example of a starting position of the block 70 is shown in FIG. 4A, where the burr 30 is disposed at the first side 20 of the sheath 11. Movement of the block 70 in a proximal direction deflects the distal end 28 toward the second side 21. One example of a deflected position of the block 70 is shown in FIG. 4B, where the burr 30 is disposed at the second side 21 of the sheath 11.

The distal end 28 of the drill bit 14 can be biased toward one side 20, 21 of the sheath 11, such as by a spring or other suitable biasing mechanism 68. In the embodiment shown in FIG. 4A-4C, a spring 68 can bias the distal end 28 toward the second side 21. In the starting position of the block 70, as shown in FIG. 4A, the spring 68 is stretched, e.g. under tension. As the block 70 moves to the deflected position shown in FIG. 4B, the spring 68 relaxes and pulls the drill bit 14 to the position where the burr 30 is disposed at the second side 21 of the sheath 11. The spring 68 or other biasing mechanism can be disposed external or internal to the sheath 11.

The drill bit 14 and sheath 11 can include a ball and socket joint 34 as previously described, with the ball 35 supporting the drill bit 14 at the proximal end 17 of the sheath 11. Optionally, the drill bit 14 and sheath 11 can be calibrated using ball 35 as previously described. The spring 68 or other biasing mechanism can be disposed proximally of the ball 35 as shown. In other embodiments, the spring 68 or other biasing mechanism can be disposed distally of the ball 35.

In certain embodiments, the assembly 10 can include a drill sheath 71 defining a tubular channel sized for insertion of the drill bit 14. The drill sheath 71 in turn is received within the tubular channel 12 of the outer sheath 11. The sheath 71 has a proximal end 72 and a distal end 73, and defines a longitudinal axis that can be generally coaxial with the longitudinal axis 29 of the drill bit 14.

The block 70 can engage the drill sheath 71 in order to deflect the drill sheath 71 internally in the outer sheath 11, and thereby deflect the drill bit 14. The block 70 may travel between the inner drill sheath 71 and outer sheath 11 to produce deflection of the distal end 73 of the drill sheath 71, in turn producing deflection of the distal end 28 of the drill bit 14, thereby moving the burr 30 relative to the sides 20, 21 of the outer sheath 11. The block 70 can have low friction with the sheaths 11, 71 in order to reduce resistance therebetween, such as by being manufactured from materials having low coefficient of friction or using lubricants. In other embodiments, the block 70 can include directly engage the drill bit 14, or otherwise be configured to deflect the drill bit 14 without the use of drill sheath 71.

During operation, the distal end 28 of the drill bit 14 can extend distally of the distal end 73 of the drill sheath 71, such that the burr 30 is fully exterior of the drill sheath 71, and the exposure of the burr 30 to the bone surface is controlled by the position of the burr 30 relative to the sides 20, 21 of the outer sheath 11.

The block 70 can be shaped to produce lateral movement of the distal end 28 of the drill bit 14 as the block 70 moves axially. In the embodiment illustrated in FIG. 4C, the block 70 is generally wedge-shaped, and has an engaging surface 74 configured to face toward the drill bit 14, or drill sheath 71. The engaging surface 74 can be inclined with respect to the axis 19 of the sheath 11. In another embodiment, the block 70 can be generally rectilinear, with an engaging surface 74 that is generally parallel to the axis 19 of the sheath 11.

The block 70 can be coupled with a linear actuator 75 for moving the block 70 axially. Examples of such linear actuators 75 comprise rack and pinion gear mechanisms, worm and helical gear mechanisms, and the like. In one embodiment shown in FIG. 4C, the linear actuator 75 can comprise a rack and pinion mechanism, including a rack 77 having teeth 78 on one side that mesh with teeth 79 on a pinion 80. The pinion 80 rotates on a shaft 81 having a fixed axis 82, and translates the rotatory motion of the shaft 81 to linear movement of the rack 77.

The block 70 is coupled with the rack 77 for linear movement therewith. The block 70 can be directly connected with the rack 77. As used herein, "directly connected with" and variations thereof is used herein in the broadest sense to mean and encompass the notions of being directly formed or integrated with, directly mounted or attached to, or otherwise directly joined. In other embodiments, the block 70 can be indirectly connected with the rack 77 in a suitable manner whereby that linear movement of the rack 77 translates to axial movement of the block 70 within the sheath 11.

As the pinion 80 rotates about the fixed axis 82, the rack 77, and therefore the block 70, translates axially. Depending on whether the pinion 80 rotates clockwise or counterclockwise about the fixed axis 82, the rack 77 can move proximally or distally within the sheath 11, resulting in proximal or distal axial translation of the block 70, as indicated by arrows 84 in FIG. 4C.

The pinion shaft 81 can be rotated via manual input (e.g. under dirt operator control) or automatic input (e.g., under automated control). For a manual input mechanism, in one embodiment, a knob 83 is rigidly connected to the pinion shaft 81 for imparting rotation thereof. Upon the operator providing manual input to the knob 83, the pinion 80 rotates. The knob 83 can be accessible from the exterior of the sheath 11. Other manual input control actuators for the pinion 80 are possible, including a lever, crank arm, and the like. For an automatic input mechanism, a motor (not shown) can be coupled with the pinion shaft 81 and provides drive input to the pinion shaft 81.

In the embodiments shown in FIGS. 1-4, the sheath 11 can be mounted or attached to the robotic arm of a robotics-assisted surgical system, such as the Mazor X Stealth™ Edition robotic guidance platform (Medtronic), the Mazor Robotics Renaissance™ System, and the ExcelsiusGPS® robotic navigation platform (Globus Medical). The assembly 10 of the embodiments shown in FIGS. 1-4 can be used with such systems. This can require that the sheath 11 be configured for connection with the robotic arm, such as by being sized with a standard sheath mount of the robotic arm.

FIGS. 5A-5B show a fifth embodiment of the assembly 10, where like elements are referred to with the same reference numerals. In the fifth embodiment, the assembly 10 comprises an adaptor 90 for indirectly mounting the sheath 11 to a sheath mount of a robotic arm. This provides the freedom for the sheath 11 to have a different diameter than a sheath typically accepted by a robotics-assisted surgical system. As such, the adaptor 90 can adapt or retrofit a standard sheath mount or robotic arm for a sheath having a different size than the standard size, including sheaths that are larger or smaller than the standard size.

In certain embodiments, the adaptor 90 includes a collar 91 that mates with a sheath mount 92 (shown in phantom line in FIG. 5) of a robotic arm. An offset arm 93 can link the collar 91 with the drill sheath 11. In the embodiment shown, the arm 93 can be integrated with the socket member 42 described embodiment with respect to the second embodiment (FIGS. 2A-2C). As such, the adaptor 90 can include the ball and socket joint 34. In other embodiments, the arm 93 can be connected elsewhere on the sheath 11, with or without a ball and socket joint.

The collar 91 can be coaxial with the sheath mount 92, and can define a collar axis 93A that is aligned with an axis of the robotic arm. Due to the offset arm 93, the sheath 11 is not coaxial with the sheath mount 92. The collar 91 can be angled relative to the sheath 11, and with the drill sheath 11 and collar 91 generally being triangulated such that the distal end 18 of the drill sheath 11 generally meets the same point as the sheath 11 would if it were directly connected with the robotic arm. As such, the collar axis 93A and the sheath axis 19 can be oblique to each other and converge at the distal tip 13 of the sheath.

In the embodiment illustrated in FIG. 5A-5B, the mechanism for manipulating the drill bit 14 can comprise the ball and socket joint 34 described above with respect to FIG. 2A. In other embodiments, any embodiment of the assembly 10 or any embodiment of the manipulation mechanism disclosed herein can comprise the adaptor 90. For example, the adaptor 90 can include the ball and socket joint 34 described with respect to FIG. 1A, the gear drive 50 described with respect to FIG. 3A or 3C, or the block 70 described with respect to FIG. 4A. Any of these mechanisms can be carried by the sheath 11 or by the offset arm 93.

In yet another embodiment, the offset arm 93 between the sheath 11 and the sheath mount 92 may carry the ball and socket joint 34. In this case, the drill bit 14 does not pass through the ball 35, and the entire sheath 11 is manipulated around the drill bit 14, rather than manipulating the drill bit 14 within the sheath 11. The motion of the sheath 11 can be calibrated in order to provide the same relative range of motion between burr 30 and the distal tip 13 described for previous embodiments.

In yet another embodiment, the offset arm 93 between the sheath 11 and the sheath mount 92 may carry a hinge point or other mechanism to control the deflection of the drill bit 14.

A method for the using the assembly 10 to drill a non-perpendicular bone surface 95 is illustrated in FIGS. 6A-6C. The method can generally apply to any embodiment of the assembly 10 disclosed herein, and their various manipulation mechanisms. For simplicity, the method is generally described with respect to the assembly 10 having a manipulation mechanism 94 shown schematically in FIGS. 6A-6C. It is understood that manipulation mechanism 94 can comprise any embodiment of manipulation mechanism disclosed herein, and will operate accordingly. Regardless of the manipulation mechanism, the drill bit 14 may travel the entire cross sectional extent of the interior channel 12 defined by the sheath 11 in order to drill the non-perpendicular bone surface 95.

The drill bit 14 is loaded to the power drill 15 or otherwise coupled with a motorized drive unit, and operably coupled with the manipulation mechanism 94 for moving the distal end 28 of the drill bit 14. The steps for coupling the drill bit 14 with the manipulation mechanism 94 may vary, depending on the configuration of the manipulation mechanism 94. For example, the drill bit 14 may be bottom-loaded into the sheath 11 and/or manipulation mechanism 94, top-loaded into the sheath 11 and/or manipulation mechanism 94, or in embodiments where the drill bit 14 is provided in two or more sections, be a combination of bottom- and top-loaded.

Once assembled, the assembly 10 is placed at target site, e.g. the non-perpendicular bone surface 95, as shown in FIG. 6A. It is noted that, in being characterized as a "non-perpendicular" bone surface 95, the bone surface 95 is non-perpendicular to the longitudinal axis 19 of the sheath 11. As such, the bone surface 95 is slanted or oblique to the longitudinal axis 19 of the sheath 11. At the target site, the distal tip 13 of the sheath 11 and burr 30 of the drill bit 14 are positioned in close proximity to the bone surface 95, while allowing for manipulation of the drill bit 14 within the sheath 11. While not shown, the assembly 10 may be inserted through a cannulated guide to the target site, e.g. the non-perpendicular bone surface 95.

Once at the target site, drilling can commence, during which the drill bit 14 rotates about its axis 29 to cut the bone surface 95. In one method, the sheath 11 is initially positioned with the distal tip 13 oriented to generally follow the slope of the non-perpendicular surface 95. For example, as shown in FIG. 6B, the first side 20 an/or tip distal edge 24 of the sheath 11 can be disposed downward on the slope of the non-perpendicular surface 95, and the second side 21 an/or tip proximal edge 23 of the sheath 11 can be disposed upward on the slope of the non-perpendicular surface 95. The drill bit 14 is initially positioned with the cutting burr 30 on the first side 20 of the sheath 11. Operation of the drill bit 14 in this position can cut the non-perpendicular surface 95 on the first side 20 of the sheath 11, as shown in FIG. 6B, and protect tissue on the second side of the sheath 11 from exposure to the drill bit 14.

During drilling, the manipulation mechanism 94 can be operated to manipulate the drill bit 14 within the sheath 11 to move the burr 30 relative to the sides 20, 21 of the sheath 11, resulting in routing or sideways cutting of the non-perpendicular surface 95 to create a flattened bone surface 96, as shown in FIG. 6C. It is noted that, in being characterized as a "flattened" bone surface 96, the bone surface 96 is generally perpendicular to the longitudinal axis 19 of the sheath 11. As such, the bone surface 95 is generally flat or normal to the trajectory of the channel 12. During drilling, the burr 30 can optionally traverse the entire cross-sectional area of the channel 12, moving in a translational, orbital, or combination path. The bone surface 96 is now prepared and acceptable for robotic deep drilling, cannulation, or other procedure. After flattening the surface, the remainder of a procedure may proceed.

Embodiments of the present invention provide a bone drill assembly, or a drill and sheath mechanism, configured to flatten a non-perpendicular surface, such as during spinal surgery or robotic spinal surgery in particular. It is understood that the embodiments of the assembly 10 or drill bit 14 disclosed herein are useable during other medical procedures as well, including any operation, surgery, or related event in which a bone surface is drilled or shaped.

It is noted that while at least one of the embodiments of the manipulation mechanisms disclosed herein are internal to the sheath 11, in other embodiments the mechanism can be external to the sheath 11, and can optionally be a separate mechanical piece. A long standard drill bit and sheath can be used (such as those found in multiple surgical applications, robotics-assisted surgical systems, robotics-assisted instrumentation or handled smart instrumentation), and the sheath can pass through or attach to a separate external mechanism to provide to lateral movement of the drill bit relative to the axis of the sheath.

Various embodiments of the present invention disclosed herein have distinct advantages over prior bone drills. In at least some embodiments, the assembly 10 includes the sheath 11 to cover and protect bystander tissue (lateral and superficial) from the drill bit 14. In at least some embodiments, the drill bit 14 can be manipulated within the inner diameter of the sheath 11. This manipulation can be manual or patterned mechanically to allow the flattening of only the bone surface in the region of interest, e.g. at a target site. In at least some embodiments, the assembly 10 remains contained within the trajectory of a robotic arm of a robotics-assisted surgical system or spinal robotic system. In at least some embodiments, the assembly 10 does not require modification of the robotic arm, robotics-assisted surgical system, or spinal robotic system.

In any of the various embodiments of the assembly 10 disclosed herein, the components of the assembly 10 can be manufactured from suitable materials known in the art using appropriate techniques, such as, but not limited to, injection molding, extrusion, additive manufacturing, 3D printing, and the like. The various embodiments of the assembly 10 disclosed herein may be disposable/one-time use, or reusable.

The term "distal" as used herein refers to that end or portion which is situated toward the bone surface, patient, or target subject, e.g. generally in a direction toward the burr 30 of the drill bit 14. The term "proximal" as used herein refers to that end or portion which is situated away from the bone surface, patient, or target subject, e.g. generally in a direction away from the burr 30 of the drill bit 14.

The term "operator" as used herein includes, unless otherwise noted, any individual who uses an embodiment of the assembly 10 or drill bit 14 disclosed herein. An operator can include, for example, physicians, surgeons, orthopedic doctors, veterinarians, nurses, technicians, etc.

The above descriptions are those of current embodiments of the invention. Various alterations and changes can be made without departing from the spirit and broader aspects of the invention as defined in the appended claims, which are to be interpreted in accordance with the principles of patent law including the doctrine of equivalents.

This disclosure is illustrative and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as alternatives.

Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property of privilege is claimed are defined as follows:

1. A bone drill assembly comprising: a sheath having a proximal end and a distal end comprising a distal tip, and defining an interior channel elongated along a longitudinal sheath axis, wherein a first side of the sheath is disposed laterally of the sheath axis in a first direction and a second side of the sheath is disposed laterally of the sheath axis in a second direction, the sheath configured to receive a drill bit having a cutting burr; and a manipulation mechanism configured to be operably coupled with the drill bit received by the sheath and configured to manipulate the drill bit within the sheath to move the cutting burr relative to the first and second sides of the sheath, the manipulation mechanism providing lateral displacement of a distal end of the drill bit with respect to the longitudinal sheath axis, wherein the distal tip of the sheath comprises an end shape that is non-perpendicular to the sheath axis, wherein the manipulation mechanism comprises a ball and socket joint including a ball configured to be connected with the drill bit received by the sheath and a socket connected with the sheath and which at least partially surrounds and receives the ball, the ball having multiple degrees of motion within the socket, and wherein position of the ball relative to the cutting burr is calibrated with a distance between the socket and the distal tip of the sheath, such that when the ball is in register with the socket, the cutting burr is located at the distal tip of the sheath.

2. The bone drill assembly of claim 1 further comprising: the drill bit configured to be inserted within the sheath, the drill bit comprising a proximal end configured for coupling with a motorized drive unit, a distal end, a drill shaft defining an axis of rotation for the drill bit, and the cutting burr at the distal end of the drill bit.

3. The bone drill assembly of claim 2, wherein the manipulation mechanism is configured to manipulate the drill bit within the sheath to move the cutting burr between:
   a first position in which a geometric center of the cutting burr is disposed between the sheath axis and the first side of the sheath; and
   a second position in which the geometric center of the cutting burr is disposed between the sheath axis and the second side of the sheath.

4. The bone drill assembly of claim 2, wherein the manipulation mechanism is configured to manipulate the drill bit within the sheath to move the cutting burr between:
   a first position in which substantially the entire cutting burr is disposed between the sheath axis and the first side of the sheath; and
   a second position in which substantially the entire cutting burr is disposed between the sheath axis and the second side of the sheath.

5. The bone drill assembly of claim 2, wherein an inner diameter of the sheath is greater than a width of the cutting burr.

6. The bone drill assembly of claim 2, wherein the manipulation mechanism is coupled to the drill bit at a location proximal to the distal end of the drill bit, and is configured to suspend the distal end of the drill bit within the interior channel of the sheath.

7. The bone drill assembly of claim 1, wherein a portion of the end shape on the first side of the sheath is distal of a portion of the end shape on the second side of the sheath in a direction along the sheath axis.

8. The bone drill assembly of claim 1, wherein the end shape is angled.

9. The bone drill assembly of claim 1, wherein the end shape comprises a tip distal edge on the first side of the sheath and a tip proximal edge on the second side of the sheath, the tip distal edge being disposed distally of the tip proximal edge in a direction along the sheath axis.

10. The bone drill assembly of claim 1, wherein the socket is formed by an open proximal end of the sheath, with the ball having a diameter larger than an inner diameter of the sheath.

11. The bone drill assembly of claim 1, wherein the manipulation mechanism is configured to move the distal end of the drill bit in at least one of:
   a straight-line path within the sheath to translate the cutting burr from the first side of the sheath to the second side of the sheath; and
   a conical path within the sheath to orbit the cutting burr from the first side of the sheath to the second side of the sheath.

* * * * *